(12) United States Patent
Pacino, II

(10) Patent No.: US 10,713,742 B1
(45) Date of Patent: Jul. 14, 2020

(54) SHARED VERIFICATION OF CREDENTIAL RECORDS

(71) Applicant: Alcides O. Pacino, II, Cedar Park, TX (US)

(72) Inventor: Alcides O. Pacino, II, Cedar Park, TX (US)

( * ) Notice: Subject to any disclaimer, the term of this patent is extended or adjusted under 35 U.S.C. 154(b) by 1141 days.

(21) Appl. No.: 14/639,806

(22) Filed: Mar. 5, 2015

Related U.S. Application Data

(60) Provisional application No. 61/951,994, filed on Mar. 12, 2014.

(51) Int. Cl.
 *G06Q 50/26* (2012.01)

(52) U.S. Cl.
 CPC .................... *G06Q 50/26* (2013.01)

(58) Field of Classification Search
 CPC ....................................... G06F 21/44
 USPC ........................................... 713/18
 See application file for complete search history.

(56) References Cited

U.S. PATENT DOCUMENTS

| | | | |
|---|---|---|---|
| 4,328,978 A | 5/1982 | McLaughlin | |
| 5,652,842 A | 7/1997 | Siegrist, Jr. et al. | |
| 5,845,254 A | 12/1998 | Lockwood et al. | |
| 6,014,631 A | 1/2000 | Teagarden et al. | |
| 6,978,268 B2 | 12/2005 | Thomas et al. | |
| 7,222,079 B1 | 5/2007 | Seare et al. | |
| 7,519,591 B2 | 4/2009 | Landi et al. | |
| 7,562,026 B2 | 7/2009 | DelMonego et al. | |
| 7,672,987 B2 | 3/2010 | Mukherjee et al. | |
| 7,698,159 B2 | 4/2010 | Metzger et al. | |
| 7,720,701 B2 | 5/2010 | Richards et al. | |
| 7,734,656 B2 | 6/2010 | Bessette et al. | |
| 7,739,123 B1 | 6/2010 | Rappaport | |
| 7,752,060 B2 * | 7/2010 | Hicks ................... | G06F 19/324 705/3 |
| 7,756,728 B2 | 7/2010 | Maughan et al. | |
| 7,949,544 B2 | 5/2011 | Miglietta et al. | |
| 8,165,897 B2 | 4/2012 | Beraja et al. | |
| 8,396,271 B2 | 3/2013 | Kanda | |
| 8,452,617 B2 | 5/2013 | Kerr et al. | |
| 8,464,162 B2 | 6/2013 | Zuber | |
| 8,495,069 B2 | 7/2013 | Friedlander et al. | |
| 8,504,380 B2 | 8/2013 | Broverman et al. | |
| 8,515,777 B1 | 8/2013 | Rajasenan | |
| 8,521,564 B1 | 8/2013 | Ciechanowski | |
| 8,527,291 B1 | 9/2013 | Kochendorfer | |
| 8,548,825 B2 | 10/2013 | Ying et al. | |
| 8,560,582 B2 | 10/2013 | Harris | |
| 8,566,115 B2 | 10/2013 | Moore | |
| 8,583,450 B2 | 11/2013 | Baker et al. | |
| 2001/0039547 A1 * | 11/2001 | Black ................ | G06F 17/30595 |

(Continued)

*Primary Examiner* — Benjamin E Lanier

(74) *Attorney, Agent, or Firm* — Jack V. Musgrove

(57) ABSTRACT

A personal experience and training (PET) records search and retrieval system allows for shared verification of credentials for a service provider such as a healthcare professional. The professional uploads a credential, and a third party can view the credential and provide verification information via a verification input tool. The verification information includes a name of a verifier, a memo field providing background details on the verifier, and a date of verification. Multiple credentials can be verified, and multiple individuals can verify a single credential. A user can view these details of the verification information through a display box.

12 Claims, 5 Drawing Sheets

(56) References Cited

U.S. PATENT DOCUMENTS

| | | |
|---|---|---|
| 2002/0077853 A1 | 6/2002 | Boru et al. |
| 2003/0036927 A1 | 2/2003 | Bowen |
| 2004/0111298 A1 | 6/2004 | Schoenberg |
| 2004/0186852 A1* | 9/2004 | Rosen .................. G06Q 30/02 |
| 2006/0253302 A1 | 11/2006 | Oster |
| 2007/0106533 A1 | 5/2007 | Greene |
| 2007/0112601 A1 | 5/2007 | Benja-Athon et al. |
| 2008/0059268 A1* | 3/2008 | Davantes ....... G06Q 10/063112 705/7.14 |
| 2008/0083023 A1* | 4/2008 | Kumar H S .......... G06Q 10/02 726/6 |
| 2008/0183497 A1 | 7/2008 | Soon-Shiong |
| 2008/0270420 A1* | 10/2008 | Rosenberg ........ G06F 17/30303 |
| 2009/0164252 A1* | 6/2009 | Morris .................. G06Q 10/00 705/3 |
| 2009/0187423 A1 | 7/2009 | Kim |
| 2010/0228564 A1 | 9/2010 | Kharraz Tavakol et al. |
| 2010/0274580 A1 | 10/2010 | Crownover et al. |
| 2011/0060737 A1 | 3/2011 | Cardella |
| 2011/0295887 A1 | 12/2011 | Palmese et al. |
| 2012/0270190 A1 | 10/2012 | Kenedy et al. |
| 2013/0282607 A1* | 10/2013 | Levine ............... G06Q 10/1053 705/321 |

\* cited by examiner

SHARED VERIFICATION OF CREDENTIAL RECORDS

CROSS-REFERENCE TO RELATED APPLICATION

This application claims priority from U.S. Provisional Patent Application No. 61/951,994 filed Mar. 12, 2014, which is hereby incorporated.

BACKGROUND OF THE INVENTION

Field of the Invention

The present invention generally relates to record keeping for credentials such as personal experience and training records, and more particularly to a method of sharing information about credential records.

Description of the Related Art

When an individual is looking for a service provider it is important to allow the individual to understand what qualifications or credentials the service provider has, such as education, training and experience, in order to assess the service provider's competency for a given matter. The individual may be a consumer of the service provider's services, or may be another entity such as a prospective employer or a researcher. For example, the service provider might be a medical doctor, and the individual might be a prospective patient, or might be a hospital administrator seeking to hire the doctor.

This assessment process is typically performed manually, often on paper. An individual has to seek out information regarding the service provider from various sources, and then seek corroboration or verification of that information to evaluate its validity.

SUMMARY OF THE INVENTION

The present invention is generally directed to a method of sharing verification of credentials for a service provider by receiving a first request from a first user to provide credential records for the service provider, providing a first display of the credential records for the service provider to the first user in response to the first request wherein the first display includes at least one credential entry having a credential title field indicating a type of credential and a verification input object related to the credential type, receiving verification information from the verification input object wherein the verification information relates to verification of the credential type, receiving a second request from a second user to provide the credential records for the service provider, and providing a second display of the credential records for the service provider to the second user in response to the second request, the second display including the credential entry having the credential title field indicating the type of credential and a verification field related to the credential type, the verification field including at least a portion of the verification information. The credential entry may be uploaded, for example by the service provider, prior to receiving the first request. The first display can include multiple credential entries each having a credential title field indicating a type of credential and a verification input object related to the respective credential type. The verification information may be first verification information, and the method further includes receiving a third request from a third user to provide credential records for the service provider, providing the first display of the credential records for the service provider to the third user in response to the third request, and receiving second verification information from the verification input object, the second verification information relating to verification of the credential type. The verification information can include a name of a verifier, a memo field providing background details on the verifier, and a date of verification by the verifier. Then the second user can make a request to view details of the verification information, and a display box is provided in the second display in response to this request, the display box containing the name of the verifier, the background details, and the date of verification.

The above as well as additional objectives, features, and advantages of the present invention will become apparent in the following detailed written description.

BRIEF DESCRIPTION OF THE DRAWINGS

The present invention may be better understood, and its numerous objects, features, and advantages made apparent to those skilled in the art by referencing the accompanying drawings.

The use of the same reference symbols in different drawings indicates similar or identical items.

DESCRIPTION OF THE PREFERRED EMBODIMENT(S)

Searching and finding information about service providers such as healthcare professionals is difficult for individuals, and expensive for organizations. Generally, most paper-based processes are inefficient when it comes to searching. This approach typically results in redundant searches and incomplete information.

Some web sites on the Internet provide more organized collections of information for certain service providers, but the veracity of this information is often questionable. When dealing with professionals it is incumbent upon the searcher to ensure that information such as professional credentials are actually valid. It can be further difficult to provide such assurances. For example, a service provider may state that he has a graduate degree from a particular university, but to be completely sure of this credential an individual has to contact the university and obtain a transcript. In several professions, there are many different credentials that a professional might have, further compounding this problem.

It would, therefore, be desirable to devise an improved method of providing verification of credential records. It would be further advantageous if the method could allow a third party to provide the verification which could then be shared in a reliable manner with other individuals. These objects are achieved in a personal experience and training (PET) records search and retrieval system embodying the present invention which allows a third-party user to provide verification information for credentials listed under a particular service provider. This verification information can be shared with other users who can then have a certain degree of confidence in the veracity of the credentials without having to go to the trouble of personally verifying them, thereby saving individuals and industries significant time and resources.

These features may be included with other features in the PET records search and retrieval system. Some embodiments of that system include a novel process for screening professionals to verify competency in relation to one or more specific tasks. In some embodiments, the system is a healthcare screening system that searches the PET records of a professional, verifies the authenticity of the PET records through a third party, and retrieves the third party-authenticated PET records of the professional. In some embodiments, the system also uses the retrieved PET records to verify the professional's competency in performing one or more specific tasks.

Embodiments of the invention described in this specification solve the efficiency problems inherent in the existing paper-based searching and screening processes by streamlining the screening process for site feasibility in clinical trials, the screening process for employment, and the process of compliance tracking of healthcare professionals.

Figure 1:
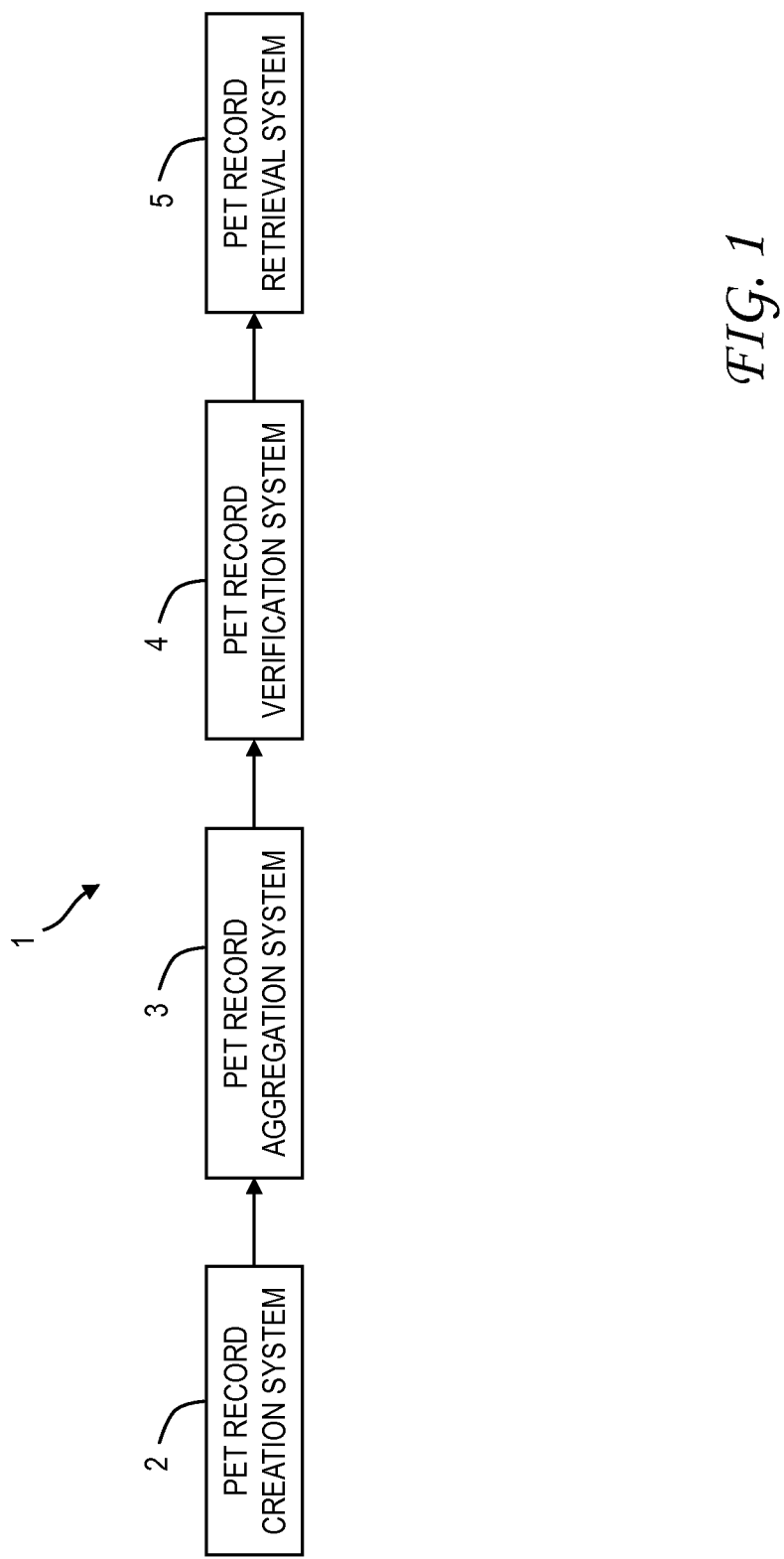
FIG. 1 is a block diagram of a personal experience and training (PET) records search and retrieval system constructed in accordance with one embodiment of the present invention.

With reference now to the figures, and in particular with reference to FIG. 1, there is depicted one embodiment 1 of a PET records search and retrieval system constructed in accordance with the present invention. PET records search and retrieval system 1 is generally comprised of a plurality of sub-systems including a set of PET record creation systems 2, a set of PET record aggregation systems 3, a set of PET record verification systems 4, and a set of PET record retrieval systems 5. In some embodiments, each set of systems comprises a single sub-system of the PET records search and retrieval system 1. In other embodiments, some of the sets of systems comprise a plurality of sub-systems of the PET records search and retrieval system 1.

The set of sub-systems shown in this figure include an example flow of operations (illustrated by arrows between the blocks) that are performed by the PET records search and retrieval system 1 in some embodiments. As shown, the system 1 first creates PET records, then transitions to another system to perform PET record aggregation (e.g., by searching for PET records associated with a particular professional being screened). Next, the system 1 verifies the aggregated PET records to make sure that the PET records are authentic and actually do relate to the professional being screened. In some embodiments, verification is performed by a third party. After verification of PET records, the system 1 transitions to the final stage in which the PET records are retrieved. While this example flow of operations provides an overview of how the PET records search and retrieval system 1 is able to efficiently perform screening of a person, in some embodiments system 1 performs one or more of the operations in a different sequence or in an adapted manner. For instance, some embodiments of system 1 may retrieve the PET aggregated records before receiving third party verification of the authenticity of the PET records, and then discard any PET records which the third party does not verify.

A system operating in accordance with the present disclosure can perform a process that may be comprised of the following steps. This list of possible steps is intended to be exemplary only and it is not intended that this list be used to limit the system or process of the present application to just these steps or requiring all of these steps. Persons having ordinary skill in the art relevant to the present disclosure may understand there to be equivalent steps that may be substituted within the present disclosure without changing the essential function or operation of the system and/or process. First, a user can search for a service provider's personal account via a proprietary global search engine. Once the service provider's account is found the user can verify the provider's identity. Shareable PET records can then be retrieved from the personal account, while ensuring that the retrieved PET records are authenticated and validated by a third party. The user can also verify that the PET records are up to date.

The various elements of the system and steps of the process in the present disclosure as presented in the figures and in this specification may be related in the following exemplary fashion. It is not intended to limit the scope or nature of the relationships between the various elements and/or steps and the following examples are presented as illustrative examples only. The step by step process allows the system to conduct a proper search, viewing and screening of professionals in healthcare.

The system of the present disclosure generally works by performing the steps in the process. These steps allow the proper verification of personal experience and training records retrieval in order to verify a person's professional competency prior to performing a task on a patient or subject. This approach to searching for personal experience and training records can retrieve the information from a series of synchronized databases via a private permission-based network.

To make the system and process of the present disclosure, a person may create, design, program, and implement a set of proprietary software applications from which this approach for screening professionals is derived and performed via one or more computing resources. In some embodiments, the computing resources are interconnected through a public data network, such as the Internet. All steps may be needed in some embodiments to properly screen a person in a particular industry. However, in other industries, the process may be adapted to screen associated professionals from within that industry. In any event, the sequential searching and verification process allows for the proper search, discovery, and retrieval of PET records via a proprietary permission-based network.

Figure 2:
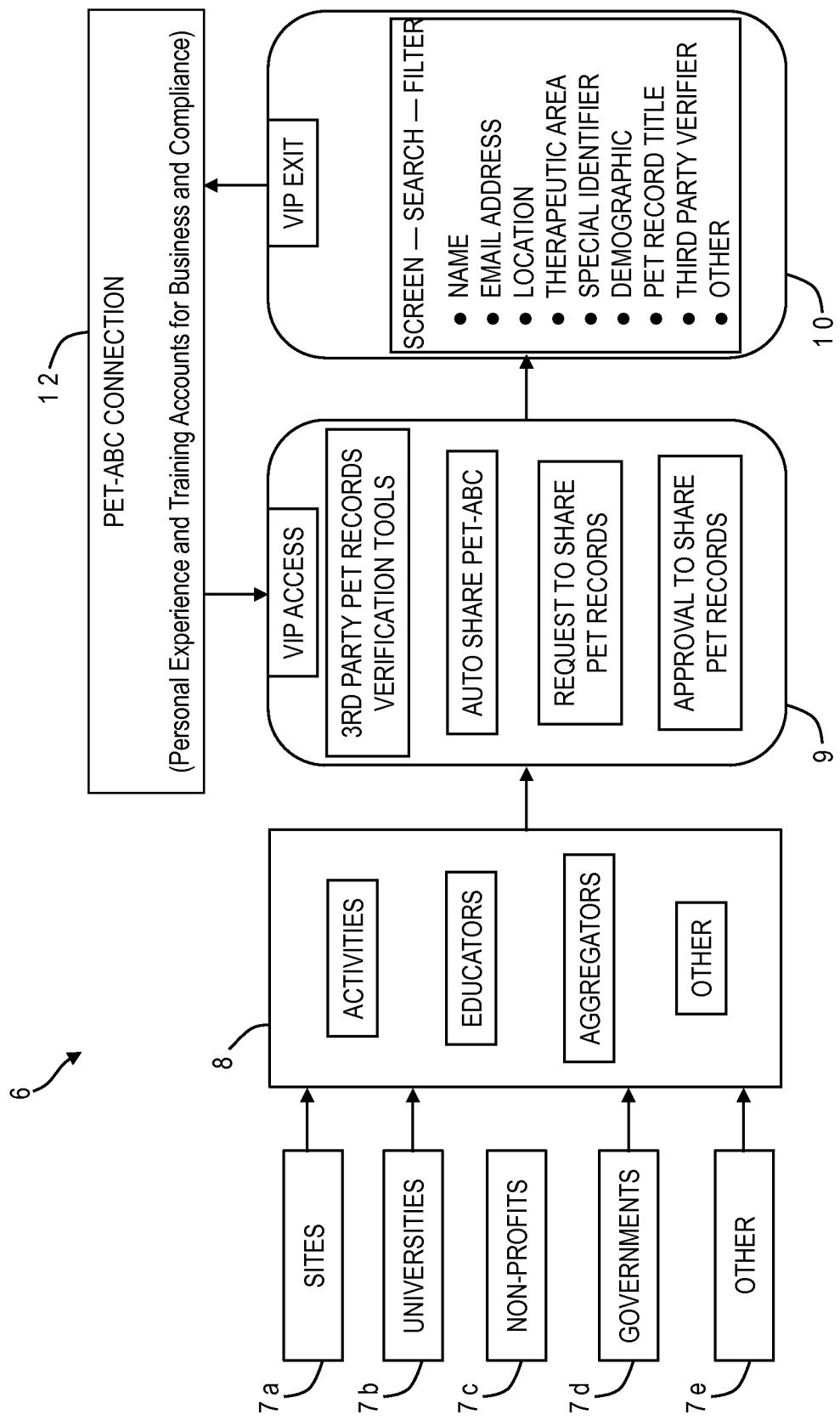
FIG. 2 is a pictorial representation of a system environment for a PET records search and retrieval system constructed in accordance with one embodiment of the present invention.

FIG. 2 conceptually illustrates a detailed system environment 6 for an integrated PET records search and retrieval system in some embodiments. As shown in this figure, environment 6 includes a plurality of connected entities, e.g., sites 7*a*, universities 7*b*, non-profit organizations 7*c*, government entities 7*d*, and other organizations or individuals 7*e*, which perform the PET record creation operations. Such PET records, when created, are aggregated at one or more sites 8 related to the professional. For instance, the professional may be involved in certain activities, educational institutions, various other entities that perform their own aggregation, etc.

The PET records search and retrieval system 1 in some embodiments then performs operations to obtain the aggregated PET records or identify locations at which the aggregated PET records may be accessed. The PET records search and retrieval system 1 then ensures that the aggregated PET records are reviewed by a third party in order to verify the authenticity and accuracy of the PET records with respect to the professional being screened. In some embodiments, this may involve VIP access 9 in relation to obtaining the PET records and/or ensuring that a third party performs the due diligence on the aggregated PET records. The VIP access 9 may accordingly include third party PET records verification tools, automated sharing of PET records via accounts for business compliance (ABC), manual requests to share PET records, and subsequent approvals to share PET records.

Finally, the PET records search and retrieval system 1 retrieves all of the aggregated PET records which have been validated by the third party. This process may involve VIP exit 10 which can perform screening operations, searching operations, and filtering operations in relation to the professional being screened and the validated PET records. Records may be screened, searched or filtered by a variety of fields including without limitation name, address (email or postal), location, therapeutic area, any special identifier, demographics, PET record title, or third-party verifier. In this manner, the PET records search and retrieval system 1 is able to efficiently search PET records, have them validated by a third party, and complete the screening process of the professional.

Additionally, the system of some embodiments may include an adapted process (similar to the processes above), which can be performed in other fields when screening for a person's competency in order to assess whether or not a person is competent enough to perform tasks. Also, some embodiments of the system are capable of producing verification records and/or certifications based on verifying competency of a professional by screening for PET records in order for an individual to be able to perform a specific set of tasks.

Figure 3:
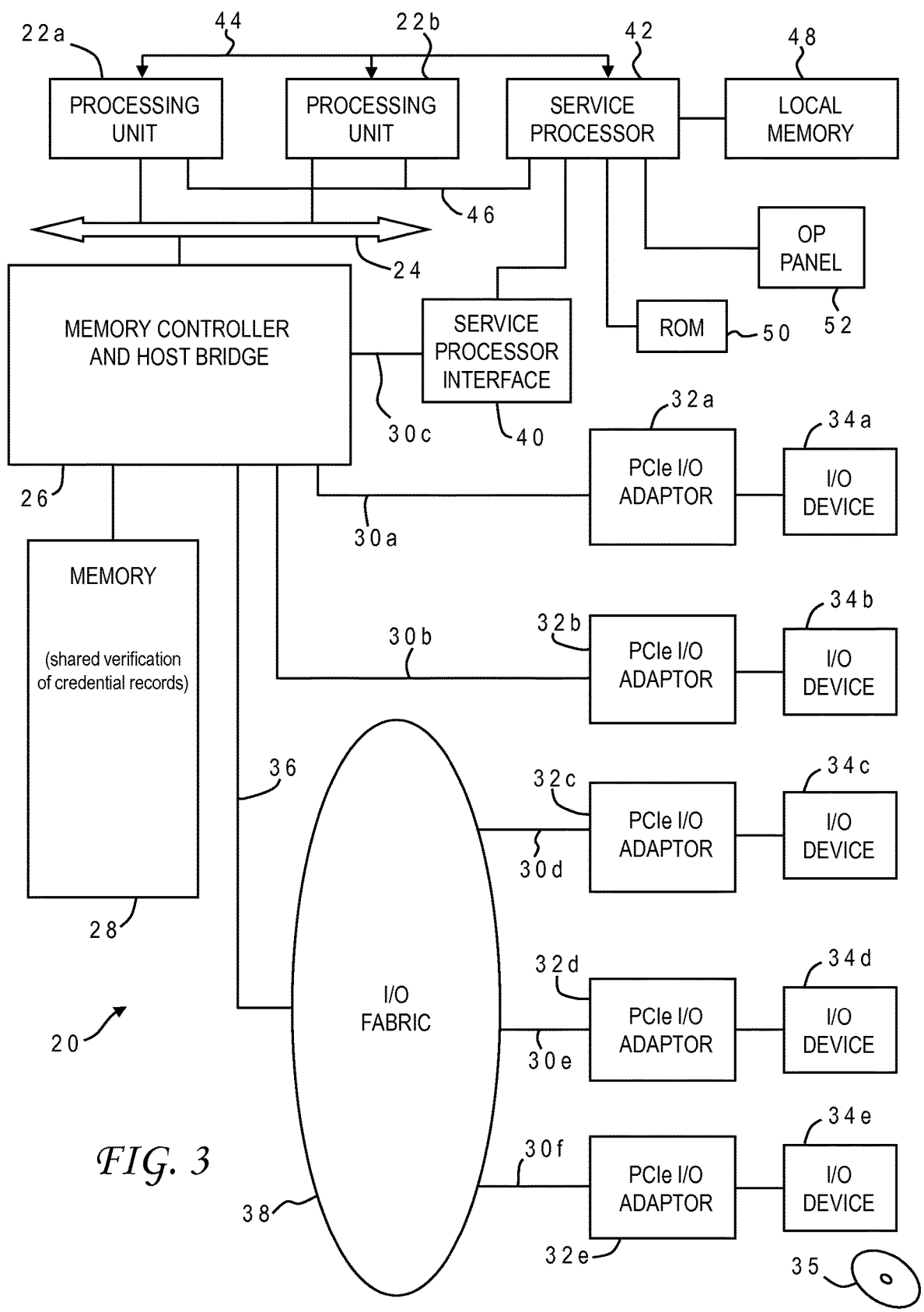
FIG. 3 is a block diagram of a computer system programmed to carry out shared verification of credential records in accordance with one implementation of the present invention.

With further reference to FIG. 3, there is depicted one embodiment 20 of a computer system in which the present invention may be implemented to carry out the shared verification of credential records such as PET records. Computer system 20 is a symmetric multiprocessor (SMP) system having a plurality of processors 22a, 22b connected to a system bus 24. System bus 24 is further connected to a combined memory controller/host bridge (MC/HB) 26 which provides an interface to system memory 28. System memory 28 may be a local memory device or alternatively may include a plurality of distributed memory devices, preferably dynamic random-access memory (DRAM). There may be additional structures in the memory hierarchy which are not depicted, such as on-board (L1) and second-level (L2) or third-level (L3) caches. System memory 28 has loaded therein an application for sharing verification of credential records in accordance with the present invention.

MC/HB 26 also has an interface to peripheral component interconnect (PCI) Express links 30a, 30b, 30c. Each PCI Express (PCIe) link 30a, 30b is connected to a respective PCIe adaptor 32a, 32b, and each PCIe adaptor 32a, 32b is connected to a respective input/output (I/O) device 34a, 34b. MC/HB 26 may additionally have an interface to an I/O bus 36 which is connected to a switch (I/O fabric) 38. Switch 38 provides a fan-out for the I/O bus to a plurality of PCI links 30d, 30e, 30f. These PCI links are connected to more PCIe adaptors 32c, 32d, 32e which in turn support more I/O devices 34c, 34d, 34e. The I/O devices may include, without limitation, a keyboard, a graphical pointing device (mouse), a microphone, a display device, speakers, a permanent storage device (hard disk drive) or an array of such storage devices, an optical disk drive which receives an optical disk 35 (one example of a computer readable storage medium) such as a CD or DVD, and a network card. Each PCIe adaptor provides an interface between the PCI link and the respective I/O device. MC/HB 26 provides a low latency path through which processors 22a, 22b may access PCI devices mapped anywhere within bus memory or I/O address spaces. MC/HB 26 further provides a high bandwidth path to allow the PCI devices to access memory 28. Switch 38 may provide peer-to-peer communications between different endpoints and this data traffic does not need to be forwarded to MC/HB 26 if it does not involve cache-coherent memory transfers. Switch 38 is shown as a separate logical component but it could be integrated into MC/HB 26.

In this embodiment, PCI link 30c connects MC/HB 26 to a service processor interface 40 to allow communications between I/O device 34a and a service processor 42. Service processor 42 is connected to processors 22a, 22b via a JTAG interface 44, and uses an attention line 46 which interrupts the operation of processors 22a, 22b. Service processor 42 may have its own local memory 48, and is connected to read-only memory (ROM) 50 which stores various program instructions for system startup. Service processor 42 may also have access to a hardware operator panel 52 to provide system status and diagnostic information.

In alternative embodiments computer system 20 may include modifications of these hardware components or their interconnections, or additional components, so the depicted example should not be construed as implying any architectural limitations with respect to the present invention. The invention may further be implemented in an equivalent cloud computing network.

When computer system 20 is initially powered up, service processor 42 uses JTAG interface 44 to interrogate the system (host) processors 22a, 22b and MC/HB 26. After completing the interrogation, service processor 42 acquires an inventory and topology for computer system 20. Service processor 42 then executes various tests such as built-in-self-tests (BISTs), basic assurance tests (BATs), and memory tests on the components of computer system 20. Any error information for failures detected during the testing is reported by service processor 42 to operator panel 52. If a valid configuration of system resources is still possible after taking out any components found to be faulty during the testing then computer system 20 is allowed to proceed. Executable code is loaded into memory 28 and service processor 42 releases host processors 22a, 22b for execution of the program code, e.g., an operating system (OS) which is used to launch applications and in particular the credential records application of the present invention, results of which may be stored in a hard disk drive of the system (an I/O device 34). While host processors 22a, 22b are executing program code, service processor 42 may enter a mode of monitoring and reporting any operating parameters or errors, such as the cooling fan speed and operation, thermal sensors, power supply regulators, and recoverable and non-recoverable errors reported by any of processors 22a, 22b, memory 28, and MC/HB 26. Service processor 42 may take further action based on the type of errors or defined thresholds.

The present invention may be implemented on other electronic computing devices including without limitation personal or hand-held electronic devices such as smartphones.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Computer system 10 carries out program instructions for a credential records system that uses novel techniques to verify and share information. Accordingly, a program embodying the invention may include conventional aspects of various record keeping tools, and these details will become apparent to those skilled in the art upon reference to this disclosure.

Figure 4:
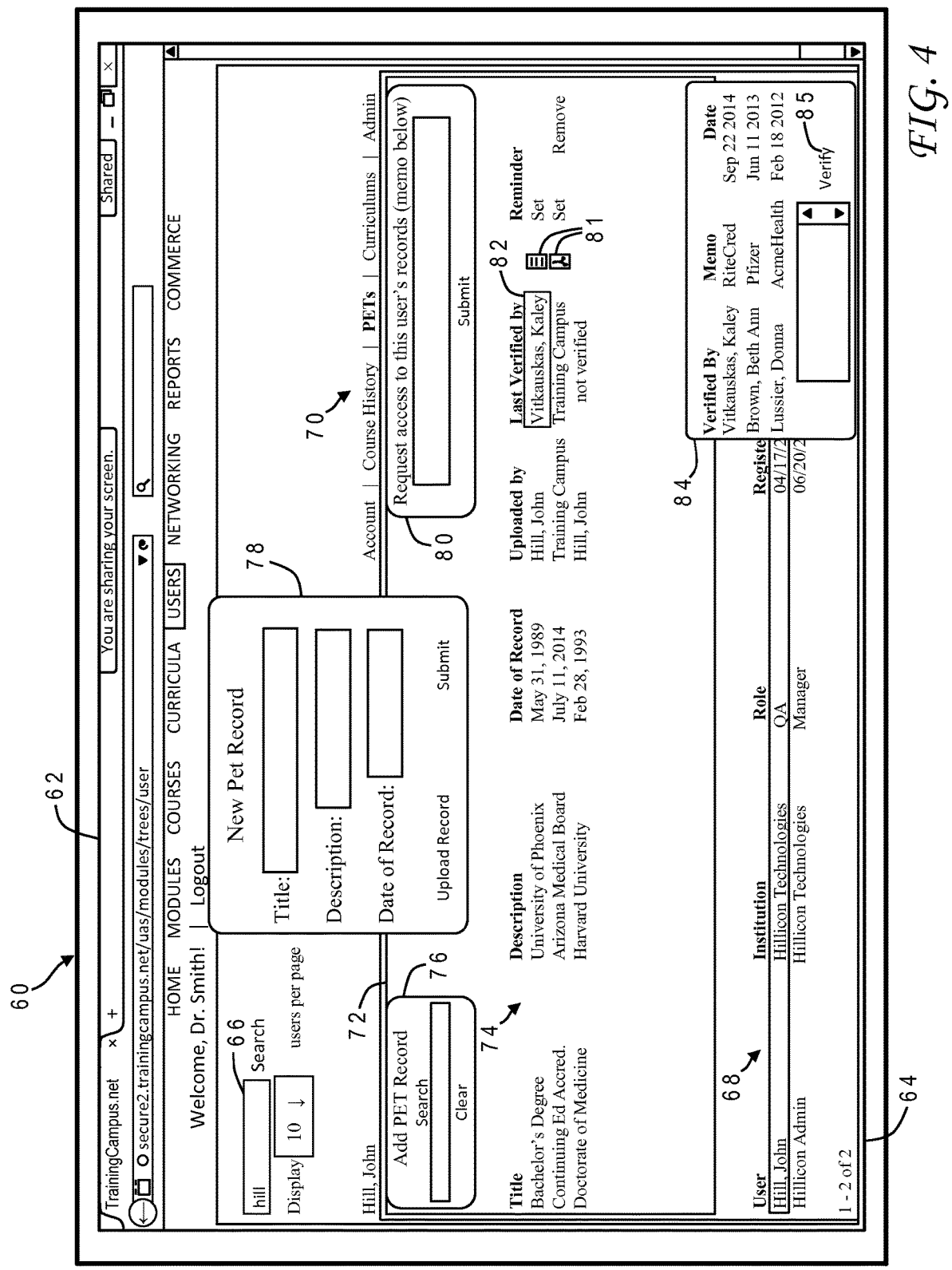
FIG. 4 is a display of a user interface including a web browser having a web page showing a list of credential records which have been verified by third parties in accordance with one implementation of the present invention.

Referring now to FIG. 4, there is depicted a screen 60 of a display device of a computer system which can be used to view credential records according to a preferred implementation. That computer system may be the same as the computer system 20 which is carrying out the server functions of maintaining credential records and providing requested credentials to a user, but in the exemplary embodiment it is a separate computer system such as a user workstation (client), although it may have a construction similar to that of computer system 20. The user workstation can be running any conventional operating system such as Windows 8, and can use any convenient application for a user interface 62, particularly a web browser such as Internet Explorer or Firefox which provide a variety of browser features. While screen 60 may be considered a "display", those skilled in the art understand that the separate computer system (server) can be considered to provide the display data without actually making it visible, i.e., "providing a display" can simply refer to the server sending out the browser page with appropriate coding according to the present disclosure, regardless of whether that page is ultimately seen on any display device.

In this example browser 62 is showing a web page 64 provided by the server ("TrainingCampus.net") which embodies PET records search and retrieval system 1. The server can provide a plurality of primary pages including "HOME", "MODULES", "COURSES", "CURRICULA", "USERS", "NETWORKING", "REPORTS", and "COMMERCE". The depicted web page 64 is the "USERS" page which can be constructed using coding such as hypertext markup language (HTML) or extensible markup language (XML). These two coding languages are not meant to be construed in a limiting manner and the coding may be carried out using any languages or protocols, including ones not yet devised.

Web page 64 preferably includes a search box 66 so a user can search for a particular individual or organization, i.e., service provider, whose credentials are desired to be seen. Further to this example the user has searched for "hill" and two results are shown in a results list 68, one for "Hill, John" and another for "Hillicon Admin". The user has selected the John Hill entry from the list (either via a touch screen or using a graphical pointing device, i.e., mouse), so page 64 includes further details regarding this service provider. Those details may be provided via a plurality of commands from a command menu 70 which includes commands denoted "Account", "Course History", "PETs", "Curriculum" and "Admin". The user has further selected the "PETS" commands as indicated by the bold typeface for that command in FIG. 4, resulting in a display of a PET record pane or frame 72 for John Hill which includes a plurality of PET records 74.

Frame 72 also includes an input object 76 which allows a user to add a new PET record for the selected service provider. In this implementation input object 76 includes a hypertext link denoted "Add PET Record" which, when activated (via touch screen or mouse) causes the server to dynamically create a dialog box 78 (this dialog box may alternatively be included with the original web page 64 as a javascript feature without displaying the dialog box until it is invoked). The "New Pet Record" dialog box 78 has various fields allowing the user to enter information relating to a credential; in this embodiment the fields include a title, a description, and a date of the credential, but other fields can be provided in alternative embodiments. When the user clicks on the "Submit" link at the bottom of dialog box 78, the information is transmitted to the server which aggregates the information with other credential records for the service provider. The system may optionally limit who is allowed to add new PET records, to accounts for individuals whose status has been authenticated or otherwise approved, e.g., the service provider himself, or an administrator for the web site (server enterprise). Frame 72 can further include a tool 80 allowing the user to request additional records of the service provider. The request can be submitted to the service provider or other party (e.g., administrator) for approval.

The list of PET records 74 shows, for each credential record, the information previously entered via dialog box 78 (title, description, and date of record) as well as additional information such as the entity who provided (uploaded) the original record, a link 81 for an uploaded electronic copy of the record (e.g., a PDF or JPEG file) and an indication of whether the record has been verified. In the illustrative implementation that indication is a name of an individual who has personally or vicariously verified the record (of the last person to verify if there are multiple verifications). If the record has not been verified by anyone the indication will instead be "not verified". This text is presented in web page 64 as a hypertext link to allow the user to see additional verification details, or allow the user to enter verification information so it can function as a verification input tool. Other display objects may be used as an input tool for verification details. While the invention contemplates that some records will be verified manually, other records can be dynamically created by the system itself (e.g., for continuing education courses), in which case the name of the verifier is a name for the system entity ("Training Campus").

When the user selects the link as indicated for example by the highlighted box 82, a display box 84 appears on the page providing the additional verification information (clicking on the "not verified" link also pulls up this window but without any verification information). Display box 84 may again be dynamically generated by the server (computer system 20) or may be included in the original web page as a javascript feature and hidden until activated. Other organizations can have the same page so if a participant is connected to multiple organizations at the same time, records can be verified by multiple organizations simultaneously. Accordingly in this implementation the additional verification information includes a list of multiple individuals who have carried out some form of verification, a memo for each verifier providing background details, and a date that the verification was considered complete. Other information can be provided in alternative implementations. Display box 84 also has a field for entering text corresponding to a memo for a new verification. Once the user has entered the verification memo she can click on the "Verify" link 85 to send the additional verification information to the system. The system can automatically provide the name of the user for the "Verified By" column as well as the current date for the "Date" column. The system may again limit verification to accounts for individuals whose status has been authenticated or otherwise approved as being appropriate for verification purposes, i.e., that the verifier herself can actually be relied on.

In the example of FIG. 4, the first credential record for John Hill is a Bachelor's Degree from the University of Phoenix, with a date for the record of May 31, 1989. John Hill himself uploaded this record, and provided an electronic copy of the record, e.g., a scan of his transcript from that university. This record has been verified by three individuals, Kaley Vitkauskas (most recently), Beth Ann Brown, and Donna Lussier. The present invention therefore provides an efficient way to screen professionals by searching for actual PET records and seeing previous verifications, thereby saving healthcare and clinical research industry time and resources.

Figure 5:
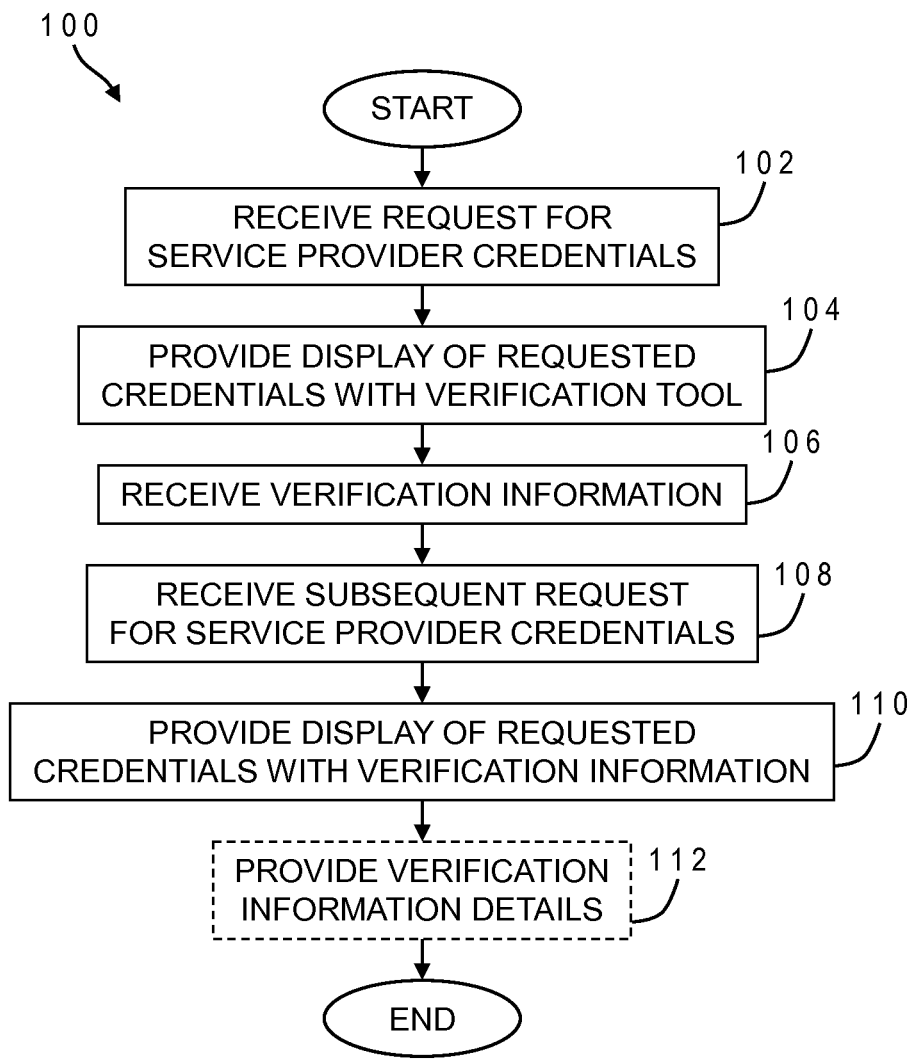
FIG. 5 is a chart illustrating the logical flow for a shared verification process in accordance with one implementation of the present invention.

The present invention may be further understood with reference to the chart of FIG. 5 which illustrates the logical flow for a shared verification process 100 in accordance with one implementation of the present invention. Process 100 begins when computer system 10 receives a request from a user for credentials of a particular service provider (102). Computer system 10 responds to the request by providing a display (e.g., web page) with the requested credentials (104). This display includes a verification input object or tool to allow the user to provide verification information. The user can use this tool to enter verification information, which is then received by the computer system (106). Thereafter, computer system 10 receives another request, i.e., from a different user, asking to see the credentials for the same service provider (108). Computer system 10 accordingly provides another display for this second user, now including the previously entered verification information (110). In this implementation the first and second displays are essentially the same web page except for the newly entered verification information. The second user can optionally request the details of the verification information, in which case the computer system provides such details (112).

Although the invention has been described with reference to specific embodiments, this description is not meant to be construed in a limiting sense. Various modifications of the disclosed embodiments, as well as alternative embodiments of the invention, will become apparent to persons skilled in the art upon reference to the description of the invention. For example, the invention has been described in the context of assessing the qualifications of healthcare professionals, but it is not so limited as it may be used for assessing credentials of any professionals or even non-professionals such as in a personal (non-commercial) setting. It is therefore contemplated that such modifications can be made without departing from the spirit or scope of the present invention as defined in the appended claims.

What is claimed is:

1. A method of sharing verification of credentials for a service provider comprising:
   receiving a first request from a first user to provide credential records for the service provider, by executing first instructions in a computer system;
   providing a first display of the credential records for the service provider to the first user in response to the first request, the first display including at least one credential entry having a credential title field indicating a type of credential and a verification input object related to the credential type, by executing second instructions in the computer system;
   receiving verification information entered using the verification input object, the verification information relating to verification of the credential type, by executing third instructions in the computer system, wherein the verification information includes at least a name of a verifier, a memo field providing background details on the verifier, and a date of verification by the verifier;
   receiving a second request from a second user to provide the credential records for the service provider, by executing fourth instructions in the computer system;
   providing a second display of the credential records for the service provider to the second user in response to the second request, by executing fifth instructions in the computer system, the second display including the credential entry having the credential title field indicating the type of credential and a verification field related to the credential type, the verification field including at least a portion of the verification information;
   receiving a third request from the second user to view details of the verification information; and
   providing a display box in the second display in response to the third request, the display box including the name of the verifier, the background details, and the date of verification.

2. The method of claim 1, further comprising receiving an upload of the at least one credential entry prior to receiving the first request.

3. The method of claim 1 wherein the first display includes multiple credential entries each having a credential title field indicating a type of credential and a verification input object related to the respective credential type.

4. The method of claim 1 wherein the verification information is first verification information, and further comprising:
   receiving a third request from a third user to provide credential records for the service provider;
   providing the first display of the credential records for the service provider to the third user in response to the third request; and
   receiving second verification information from the verification input object, the second verification information relating to verification of the credential type.

5. A computer system comprising:
   one or more processors which process program instructions;
   a memory device connected to said one or more processors; and
   program instructions residing in said memory device for sharing verification of credentials for a service provider by receiving a first request from a first user to provide credential records for the service provider, providing a first display of the credential records for the service provider to the first user in response to the first request wherein the first display includes at least one credential entry having a credential title field indicating a type of credential and a verification input object related to the credential type, receiving verification information entered using the verification input object wherein the verification information relates to verification of the credential type and the verification information includes at least a name of a verifier, a memo field providing background details on the verifier, and a date of verification by the verifier, receiving a second request from a second user to provide the credential records for the service provider, providing a second display of the credential records for the service provider to the second user in response to the second request wherein the second display includes the credential entry having the credential title field indicating the type of credential and a verification field related to the credential type, the verification field including at least a portion of the verification information, receiving a third request from the second user to view details of the verification information, and providing a display box in the second display in response to the third request, the display box including the name of the verifier, the background details, and the date of verification.

6. The computer system of claim 5 wherein said program instructions further receive an upload of the at least one credential entry prior to receiving the first request.

7. The computer system of claim 5 wherein the first display includes multiple credential entries each having a credential title field indicating a type of credential and a verification input object related to the respective credential type.

8. The computer system of claim 5 wherein:

the verification information is first verification information; and said program instructions further receive a third request from a third user to provide credential records for the service provider, provide the first display of the credential records for the service provider to the third user in response to the third request, and receive second verification information from the verification input object, the second verification information relating to verification of the credential type.

9. A computer program product comprising:

a computer readable storage medium; and program instructions residing in said storage medium for sharing verification of credentials for a service provider by receiving a first request from a first user to provide credential records for the service provider, providing a first display of the credential records for the service provider to the first user in response to the first request wherein the first display includes at least one credential entry having a credential title field indicating a type of credential and a verification input object related to the credential type, receiving verification information entered using the verification input object wherein the verification information relates to verification of the credential type and the verification information includes at least a name of a verifier, a memo field providing background details on the verifier, and a date of verification by the verifier, receiving a second request from a second user to provide the credential records for the service provider, providing a second display of the credential records for the service provider to the second user in response to the second request wherein the second display includes the credential entry having the credential title field indicating the type of credential and a verification field related to the credential type, the verification field including at least a portion of the verification information, receiving a third request from the second user to view details of the verification information, and providing a display box in the second display in response to the third request, the display box including the name of the verifier, the background details, and the date of verification.

10. The computer program product of claim 9 wherein said program instructions further receive an upload of the at least one credential entry prior to receiving the first request.

11. The computer program product of claim 9 wherein the first display includes multiple credential entries each having a credential title field indicating a type of credential and a verification input object related to the respective credential type.

12. The computer program product of claim 9 wherein:

the verification information is first verification information; and said program instructions further receive a third request from a third user to provide credential records for the service provider, provide the first display of the credential records for the service provider to the third user in response to the third request, and receive second verification information from the verification input object, the second verification information relating to verification of the credential type.

\* \* \* \* \*